United States Patent [19]

Stephens

[11] Patent Number: 4,572,204
[45] Date of Patent: Feb. 25, 1986

[54] PRESSURE DOME WITH COMPLIANT CHAMBER
[75] Inventor: Thomas P. Stephens, Boxford, Mass.
[73] Assignee: Hewlett-Packard Company, Palo Alto, Calif.
[21] Appl. No.: 591,728
[22] Filed: Mar. 21, 1984
[51] Int. Cl.⁴ .............................................. A61B 5/02
[52] U.S. Cl. .................... 128/675; 128/748; 73/707
[58] Field of Search ................ 128/672–673, 128/675, 748; 73/707

[56] References Cited
U.S. PATENT DOCUMENTS
3,915,008  10/1975  Silverman et al. ................ 73/707
4,185,641   1/1980  Minior et al. ................... 128/675
4,398,542   8/1983  Cunningham et al. ............. 128/675

OTHER PUBLICATIONS
PCT/US81/00298; WO8102511; Reynolds, 9-1981.

Primary Examiner—Lee S. Cohen
Assistant Examiner—Angela D. Sykes
Attorney, Agent, or Firm—Donald N. Timbie

[57] ABSTRACT

A pressure dome in which the wall forming the cavity containing fluid under a pressure that is to be measured has such a low compliance as to prevent expansion or contraction of the base of the dome resulting from changes in its temperature from causing the diaphragm of a transducer coupled thereto from buckling.

6 Claims, 9 Drawing Figures

PRESSURE DOME WITH COMPLIANT CHAMBER

BACKGROUND OF THE INVENTION

This invention relates to improvements in pressure domes used for coupling the blood pressure of a patient to a transducer that generates an electrical signal corresponding to the pressure. Domes used for this purpose are generally comprised of a plastic base, a wall that is usually circular having its foot adjoining the base so as to form a cavity, a flexible membrane sealed to the top of the wall so as to close the cavity, and ports extending through said base into said cavity so that the cavity can be filled with fluid.

One type of transducer with which such a pressure dome can be used is comprised of a body having a cylindrical space formed in one surface thereof and a resilient diaphragm adhered to that surface so as to close the space. An aperture may be provided that extends through the body so as to communicate ambient air pressure to the space. The bottom of the cylindrical space and the inner surface of the diaphragm are coated with conductive material so as to form plates of a capacitor having the air in the space as a dielectric. The transducer is generally contained in a pocket formed within a transducer housing. In operation, the pressure dome and the transducer housing are clamped together so that the top of the wall of the dome is in contact with the outer surface of the diaphragm around the periphery of the cylindrical space in the body of the transducer and the membrane is in intimate contact with the diaphragm. As the pressure of fluid in the cavity of the dome increases and decreases, it is applied via the flexible membrane to the resilient diaphragm so as to cause the latter to move toward and away from the bottom of the cavity in the transducer body and thereby increase and decrease the capacitance of the capacitor. Electrical connections couple the capacitor to a circuit that converts these changes in capacitance to a signal corresponding to the fluid pressure.

It has been found that in domes of the prior art variations in the temperature of the base of the pressure dome caused by changes in the temperature of the ambient air or of the fluid within the cavity of the dome cause large radial forces in the base of the wall that are translated to its top. The diaphragm of the transducer generally has a much lower thermal expansion than the plastic base and therefore does not expand and contract at the same rate as the base. As will be explained, this may cause the diaphragm of the transducer to buckle up or down so as to change the capacitance of the capacitor and cause the pressure signal to be in error. If the portion of the radial force translated to the top of the wall exceeds the force of friction between the membrane and the diaphragm in the area that is coextensive with the top of the wall, the top of the wall will slide to a different location and cause an error in the pressure signal or a zero shift. Furthermore, movement of the top of the wall with respect to the diaphragm introduces errors in subsequent pressure readings because the top of the wall does not revert to its original position on the diaphragm when the temperature of the base regains its initial value.

BRIEF SUMMARY OF THE INVENTION

In accordance with this invention, the wall forming the cavity of the pressure dome is made so compliant that the portion of the radial forces applied to its base that is translated to its top is substantially reduced. Consequently, the buckling of the transducer diaphragm and the sliding of the top of the wall with respect to the diaphragm are substantially reduced. The wall in one previous pressure dome had an inner diameter of 0.90 inch, a height of 0.106 and a thickness of 0.1 inch and was made of a rigid plastic such as polycarbonate. The ratio of the height of the wall to its thickness was therefore 1.06. This wall had a very low compliance and translated nearly all of the radial forces at its base to its top. A preferred way of providing the desired amount of compliance is to increase the ratio of the height to the width of a wall made of rigid material. Good results have been attained with a circular wall made of polycarbonate having an inner diameter of 0.94 inch, a height of 0.106 inch and a thickness of 0.025 inch. The ratio of the height of this wall to its thickness was 4.2. An even thinner wall of this height would be desired but this would be difficult to obtain with a molding process and machining or adding a separate piece would be too expensive. It is thought that good results can be attained with the above-mentioned ratios between 10 and 2.5.

Another way of increasing the compliance is to construct the wall with flexible material, but this has the effect of reducing the high frequency response because the material expands and contracts too easily.

DETAILED DESCRIPTION OF THE INVENTION

In all figures of the drawings, identical components are designated in the same way, and the cavities and spaces are understood to be circular. In the interest of clarity, no electrical connections are shown.

Figure 1A:
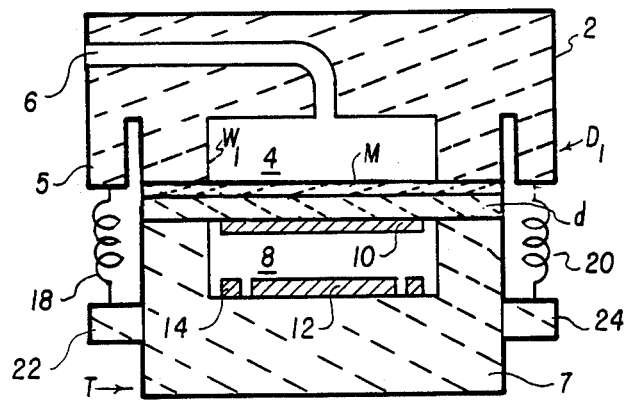
FIGS. 1A, 1B and 1C are planes at the cross-sections respectively illustrating the conditions prevailing in a pressure dome of the prior art in situations where its base is not expanded or contracted, is expanded and is contracted.

FIG. 1A illustrates a prior art pressure dome $D_1$ clamped to a transducer T. The dome $D_1$ is shown as being comprised of a base 2 to which the foot of an annular wall $W_1$ is joined so as to form a cavity 4. A port 6 and another identical port, not shown, provide means for attaching a catheter and filling the catheter and the cavity 4 with fluid. A membrane M is cemented to the bottom of the wall $W_1$ so as to close off the cavity 4, and an annulus 5 surrounding the wall $W_1$ is joined to the base 2.

The transducer T has a body 7 with a cylindrical space 8 formed therein and a diaphragm d that is attached to the body 7 so as to cover the space 8. The undersurface of the diaphragm d is coated with a layer 10 of conductive material, and the bottom of the cylindrical space 8 is coated with a layer 12 of conductive material that, although not shown in this view, is in the form of a circle and a layer 14 of conductive material that is spaced from the layer 12. The layer 14 is in the form of an annulus but this is not shown in FIG. 1A.

The pressure dome $D_1$ and the transducer T can be clamped together in any suitable manner as, for example, by a spring structure such as that shown in U.S. Pat. No. 4,185,641. The latter is schematically represented by the respective connections of tension springs 18 and 20 between the annulus 5 on the pressure dome $D_1$ and projections 22 and 24 on the transducer T.

Figure 1B:
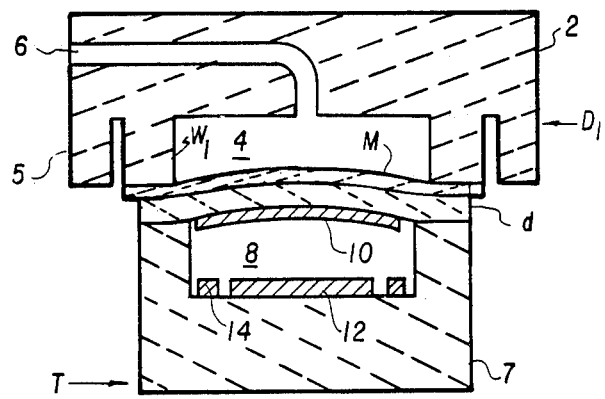

FIG. 1B is an illustration of the prior art pressure dome $D_1$ of FIG. 1A and the transducer T with the base 2 of the dome $D_1$ radially expanded. Because it is attached to the base 2, the foot of the annular wall $W_1$ is also radially expanded and because the wall $W_1$ has no little compliance, its top is radially expanded by a like amount. Because the outward radial forces at the top of the wall $W_1$ are so great, they overcome the force of friction between the membrane M and the diaphragm d in the area that is coextensive with the top of the wall $W_1$ and cause the top of the wall $W_1$ to slide outwardly with respect to the diaphragm d as indicated. The outward radial force thus exerted by the top of the wall $W_1$ on the diaphragm d creates moments about the edge of the cylindrical space 8 that cause the diaphragm d to buckle upward as shown so as to increase the separation between the capacitor plate 10 and the capacitor plates 12 and 14. This causes an erroneous decrease in the pressure signal.

Figure 1C:
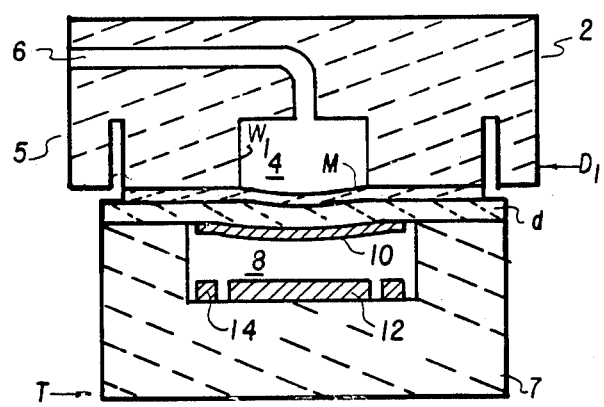

FIG. 1C is an illustration of the prior art pressure dome $D_1$ of FIG. 1A in combination with the transducer T with the base 2 of the dome $D_1$ radially contracted. Again, the compliance of the wall $W_1$ is so low that its top contracts by a like amount to the position shown. The inward radial forces exerted on the diaphragm d cause it to buckle downward so as to decrease the separation between the capacitor plate 10 and the capacitor plates 12 and 14 and cause an erroneous increase in the pressure signal.

As previously noted, the ratio of the height to the width for the annular wall $W_1$ of the prior art dome $D_1$ was 1.06:1. Good results were obtained in accordance with this invention by making the ratio 4.2:1. Ideally, the ratio should be greater than this, as much as 10:1. The lowest ratio having any significant advantage is considered to be 2.5:1. For reasons not associated with the invention, the height of the wall was limited so that the desired increase in ratio could only be attained by making the annular wall $W_2$ thinner than the 0.1 inch previously referred to. However, the desired ratio could be obtained by increasing the height. Whereas this could be attained by machining or making the wall from a separate piece, the added expense was considered to be too great for a dome that is an inexpensive disposable item. This data was achieved with domes made from polycarbonate having a flexural modulus of elasticity of $0.32 \times 10^6$ psi. Material having a modulus of elasticity of $0.15 \times 10^6$ and $0.7 \times 10^6$ psi would work satisfactorily.

Figure 2A:
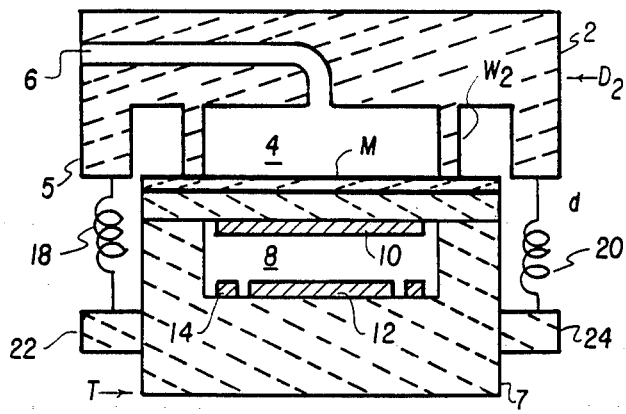
FIGS. 2A, 2B and 2C are planes at the cross-sections respectively illustrating the conditions prevailing in a pressure dome having a wall of rigid material constructed in accordance with this invention in situations where its base is not expanded or contracted, is expanded and is contracted.

FIG. 2A illustrates the combination of a pressure dome $D_2$ constructed in accordance with this invention and the transducer T with the base 2 neither expanded or contracted. The dome $D_2$ is the same as the dome $D_1$ except for the fact that its annular wall $W_2$ is more compliant than the wall $W_1$ because the ratio of its height to its thickness is greater.

Whether or not the top of the annular wall $W_1$ will change its position with respect to the periphery of the cylindrical space 8 as shown in FIGS. 1B and 1C theoretically depends on the force with which the springs 18 and 20 bring the dome $D_1$ and the transducer T together, but forces resulting from thermal expansion are generally so great as to require the forces exerted by the springs to be impracticably large if slippage is to be prevented. Furthermore, springs capable of providing such a force would be expensive and would require the operator to exert an impracticably large force when coupling and uncoupling the dome $D_1$ from the transducer T. In any event, whereas slippage in itself causes changes in the output signal attained from the transducer, the buckling up and down respectively shown in FIG. 1B and FIG. 1C would still occur.

Figure 2B:
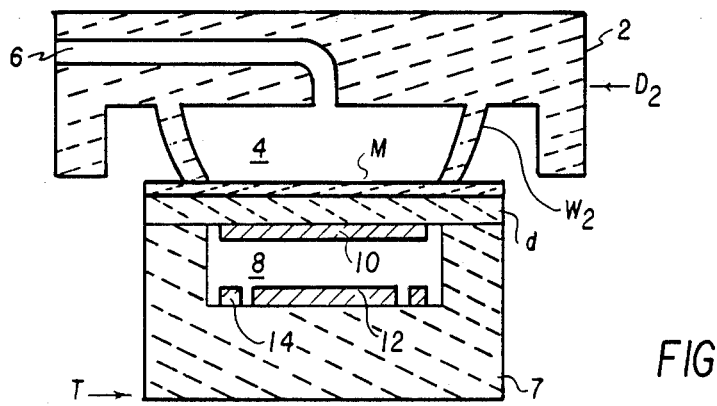
Figure 2C:
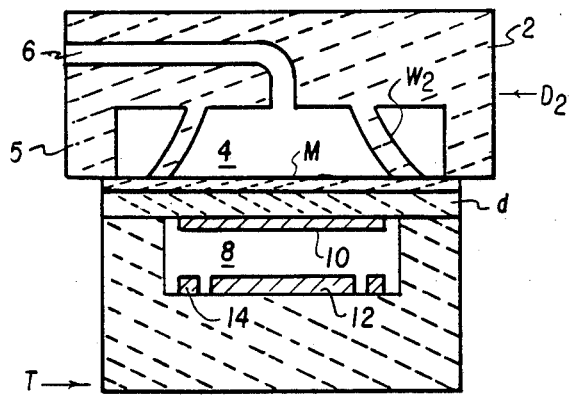

When the base 2 and therefore the foot of the wall $W_2$ expand outwardly as shown in FIG. 2B, the wall $W_2$ of this invention is so compliant that it bends, thus making the outward radial forces between the membrane and the transducer diaphragm in an area coextensive with the top of the wall less than the forces of friction that are attained with reasonable forces clamping the dome $D_2$ and the transducer T together. Under this condition, no slippage occurs. Furthermore, the radial forces exerted between the membrane M and the diaphragm d in the area that is coextensive with the top of the wall $W_2$ are so small as not to cause the diaphragm d to buckle. FIG. 2C illustrates what happens when the base 2 of the pressure dome of this invention contracts. Because of its higher compliance, the wall $W_2$ bends as shown so that the inward radial forces are too small for slippage to occur or to cause the diaphragm d to buckle. Thus, when the preferred pressure dome $D_2$ is used, the expansion or contraction of the base 2 of the pressure dome has no significant effect on the pressure signal. The compliance of the wall is such that, when changes in temperature of between 59° F. and 104° F. occur in fluid contained in the cavity or in the air temperature, the top of the wall remains stationary with respect to the pressure sensitive surface.

Figure 3A:
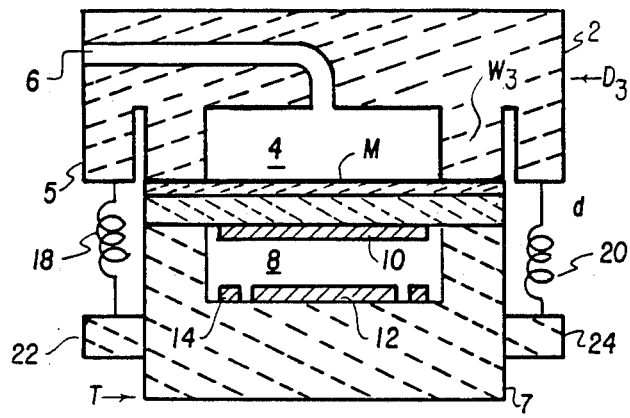
FIGS. 3A, 3B and 3C are planes at the cross-sections respectively illustrating the conditions prevailing in a pressure dome having a wall of flexible material in situations where its base is not expanded or contracted, is expanded and is contracted.
Figure 3B:
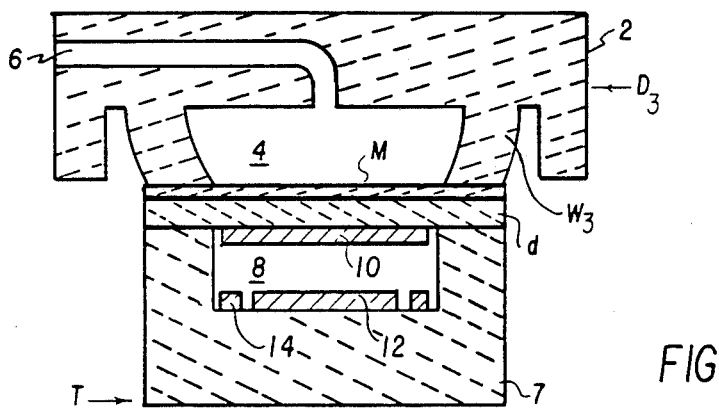
Figure 3C:
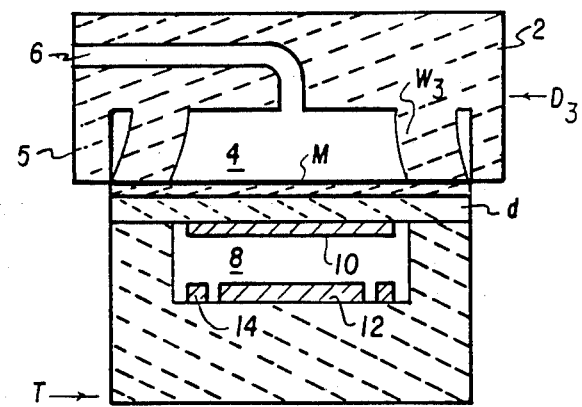

FIGS. 3A, 3B and 3C illustrate the action that takes place when a pressure dome $D_3$ is used that differs from the dome $D_1$ in that its annular wall $W_3$ is as thick as the wall $W_1$ but is made of flexible material such as rubber rather than a rigid material so that it bends in much the same way as the wall $W_2$ when the base 2 expands or contracts. But, as previously mentioned, the expansion and contraction of the flexible material decreases the high frequency response.

What is claimed is:

1. A pressure dome for communicating blood pressure to a transducer, comprising
   a base,
   a wall having a foot being attached to said base so as to form a cavity,
   a membrane adhered to the top of said wall so as to close said cavity,
   ports communicating with said cavity,
   said wall having such low compliance that most of the radial forces caused by the base expanding or contracting are not transmitted to its top.

2. A pressure dome as set forth in claim 1 wherein said wall is made of polycarbonate.

3. A pressure dome as set forth in claim 1 wherein said wall is made of flexible material.

4. A pressure dome as set forth in claim 1 wherein said wall is comprised of polycarbonate and is 0.025 inch wide and 0.106 inch high.

5. A pressure dome as set forth in claim 1 wherein the ratio of the height of the wall to its thickness is between 10 and 2.5 and the modulus of elasticity in bending of the material from which the wall is made is between $0.15 \times 10^6$ and $0.7 \times 10^6$ psi.

6. In combination,
(a) a pressure dome comprising a base,
    a wall having a foot, its foot being sealed to said base so as to form a cavity,
    ports communicating between said cavity and respective points outside the dome, and
    a membrane adhered to the top of said wall so as to be close said cavity,
(b) a transducer having a pressure sensitive surface in contact with said membrane, and
(c) means for holding said transducer and dome together so as to establish a predetermined force of 2 to 8 pounds between said membrane and said pressure sensitive surface, the static coefficient of friction between said membrane and said pressure sensitive surface being between 0.5 and 0.2,
    the compliance of said wall being such that, when changes in temperature of between 59° F. and 104° F. occur in fluid contained in said cavity or in the air temperature, the top of said wall remains stationary with respect to said pressure sensitive surface.

* * * * *